United States Patent
van der Woude et al.

(10) Patent No.: US 10,317,389 B2
(45) Date of Patent: Jun. 11, 2019

(54) REAL-TIME ROPE MONITORING

(71) Applicant: IHC Holland IE B.V., Sliedrecht (NL)

(72) Inventors: Frederik Benjamin van der Woude, Culemborg (NL); Jurgen Arjan Zijlmans, Barendrecht (NL)

(73) Assignee: IHC Holland IE B.V., Sliedrecht (NL)

(*) Notice: Subject to any disclaimer, the term of this patent is extended or adjusted under 35 U.S.C. 154(b) by 221 days.

(21) Appl. No.: 15/304,534

(22) PCT Filed: Apr. 15, 2015

(86) PCT No.: PCT/NL2015/050251
§ 371 (c)(1),
(2) Date: Oct. 17, 2016

(87) PCT Pub. No.: WO2015/160254
PCT Pub. Date: Oct. 22, 2015

(65) Prior Publication Data
US 2017/0045493 A1 Feb. 16, 2017

(30) Foreign Application Priority Data
Apr. 16, 2014 (NL) .................................. 2012634

(51) Int. Cl.
*G01N 33/36* (2006.01)
*B66B 7/12* (2006.01)
(Continued)

(52) U.S. Cl.
CPC ............ *G01N 33/36* (2013.01); *B66B 7/1215* (2013.01); *B66D 1/54* (2013.01); *B66C 13/10* (2013.01); *B66C 13/16* (2013.01)

(58) Field of Classification Search
CPC ...... G01N 33/36; B66B 7/1215; B66C 13/10; B66C 13/16; B66D 1/54
See application file for complete search history.

(56) References Cited

U.S. PATENT DOCUMENTS 6,923,065 B2 * 8/2005 Smith .................. B66B 7/1215
324/535
8,807,286 B2 * 8/2014 Puranen ................ B66B 5/0018
187/391
(Continued)

FOREIGN PATENT DOCUMENTS

CN 1625521 A 6/2005
EP 0845672 A1 6/1998
(Continued)

OTHER PUBLICATIONS

Olav Vennemann et al.; Bending Fatigue Tests Using a Suitable NDT Method to Determine Lifetime of Large Diameter Wire Ropes for Offshore Lifting Applications; Proceedings of the ASME 27th International Conference on Offshore Mechanics and Arctic Engineering, Jun. 15-20, 2008, Estoril, Portugal.
(Continued)

*Primary Examiner* — Elias Desta
(74) *Attorney, Agent, or Firm* — N.V. Nederlandsch Octrooibureau; Catherine A. Shultz; Tamara C. Stegmann

(57) ABSTRACT

A system to monitor and analyze a multi-strand rope includes a rope data sensor to collect data regarding the physical state of the rope; one or more usage sensors to collect data regarding the usage of the rope; a position measurement device to measure the position of the rope; and a computer system connected to the rope data sensor, the one or more usage sensors and the position measurement device to correlate the collected data and position measurement to give real-time data on the status of the rope at one or more sections.

20 Claims, 2 Drawing Sheets

(51) Int. Cl.
  *B66D 1/54* (2006.01)
  *B66C 13/10* (2006.01)
  *B66C 13/16* (2006.01)

(56) References Cited

U.S. PATENT DOCUMENTS 9,927,384 B2 * 3/2018 Lehtinen .................. B66B 19/02
9,995,714 B2 * 6/2018 Silvo ........................ B66C 15/06

FOREIGN PATENT DOCUMENTS

| WO | 2004/022469 A1 | 3/2004 |
| WO | 2005/040028 A1 | 5/2005 |
| WO | 2005/095250 A1 | 10/2005 |
| WO | 2007/116884 A1 | 10/2007 |
| WO | 2010/092619 A1 | 8/2010 |
| WO | 2010/098756 A1 | 9/2010 |

OTHER PUBLICATIONS

Office Action in related Chinese patent application (EN translation).

* cited by examiner

REAL-TIME ROPE MONITORING

BACKGROUND

Multi-strand ropes are used in many different applications for offshore and onshore projects, and must work safely throughout their life. As these ropes are often used for lifting operations, they can be subject to extensive bending and wear. Ropes used in offshore operations, where lifting equipment can be operating at depths of 2-3 km, are especially subject to wear and fatigue issues due to active heave compensation ("AHC") systems that are typically used for these offshore operations.

When ropes start to wear, individual strands making up the rope can break, thereby decreasing the cross-sectional area and strength of the rope and increasing the chances of a catastrophic incident or failure of the rope. Often these broken strands are inner strands, and therefore cannot be seen by a simple visual inspection. To inspect the entire rope (including the inside), a device which measures the cross-sectional area of the rope can be connected around the rope. The entire rope is then typically run through the device, and the cross-sectional area measurements are used to make an assessment of whether the rope needs replacement. Such a device is described in EP0845672 A1, which uses a magnetic testing device for obtaining a damage index of a rope by passing the rope through the device. The device includes sensors to detect local faults (e.g., nicked or broken wires) and sensors to detect the loss of metallic area, for example, from wear or corrosion. A real-time indication of a damage level of the rope is produced on a hand-held readout unit from processing the data from local fault sensors and loss of metallic area sensors (as well as a length transducer to reference the local faults) and display the damage index. Other similar devices for detecting a defect in a rope can be found in WO201/098756 A1, WO2010/092619 A1, and WO 2004/022469. Each of these disclose devices for detecting a defect in an elevator cable by running the cable through the detection device to detect a weakness or failing in the cable and the relevant location. Each of these devices takes a measurement of the existing state of the rope or cable at only a moment in time to make a determination regarding defects or damage from this measurement. None sense and/or store usage data over normal operations.

If the rope or cable does not need immediate replacement, the area measurements are often used to recommend that the rope be replaced after a specific time period. The time period is typically a conservative estimate based on classification society guidelines to guarantee the safety of the systems and the state of the rope at the time of inspection.

SUMMARY

A system to monitor and analyze a multi-strand rope includes a rope data sensor to collect data regarding the physical state of the rope; one or more usage sensors to collect data regarding the usage of the rope; a position measurement device to measure the position of the rope; and a computer system connected to the rope data sensor, the one or more usage sensors and the position measurement device to correlate the collected data and position measurement to give real-time data on the status of the rope at one or more sections.

Such a system can provide for the real-time monitoring and/or analysis of a rope during operations. This real-time monitoring and/or analysis can allow for knowledge about the condition of the rope at one or more sections, and can be used to better predict the status and condition of the rope after future operations and to plan maintenance and/or replacement operations.

According to an embodiment, the computer system comprises one or more processors and/or databases for storing and/or processing data.

According to an embodiment, the rope data sensor senses one or more of the cross-sectional area of the rope and the volume of the rope.

According to an embodiment, the data regarding the usage of the rope includes one or more of the following: bending of the rope, tension in the rope, temperature of the rope, diameter of the rope and shape of the rope.

According to an embodiment, the position measurement device is a measuring wheel or a contactless measuring system.

According to an embodiment, the computer system uses the data and the status to predict a failure of at least a section of the rope.

According to an embodiment, the computer system uses the data and the status to plan maintenance for at least a section of the rope According to an embodiment, the one or more usage sensors comprises a temperature sensor, a load sensor, a bending sensor, and/or a diameter sensor.

According to an embodiment, the database includes information regarding the historic usage, the historic state and the current state for one or more sections of the rope.

According to an embodiment, the rope is a wire rope. Optionally, the rope is a steel wire rope.

According to an embodiment, the rope is a fiber rope.

According to an embodiment, the computer system comprises a user interface.

According to an embodiment, the computer system comprises a data input for inputting data into system.

According to a further aspect, a method for real-time monitoring and analysis of a rope includes measuring and collecting physical property data for the rope; measuring and collecting usage data for the rope; measuring the position of the rope; and correlating the physical property data, the usage data and the position to give a real-time measurement of the status and event history of the rope at one or more sections.

According to an embodiment, the step of measuring and collecting physical property data for the rope comprises measuring and collecting cross-sectional area data for the rope; and/or measuring and collecting elongation or creep data for the rope.

According to an embodiment, the step of measuring and collecting usage data for the rope comprises using one or more sensors to measure and collect data related to one or more of the following: bending of the rope, tension in the rope, temperature of the rope, diameter of the rope and shape of the rope.

According to an embodiment, the method further comprises storing and/or processing the data in a computer system.

According to an embodiment, the method further comprises predicting when at least a section of the rope will fail based on the physical property data, the usage data and position.

According to an embodiment, the step of predicting when at least a section of the rope will fail based on the physical property data, the usage data and position comprises comparing the physical property data for the rope with a predetermined failure threshold; and predicting when this threshold will be reached based on collected usage data and physical property data.

DETAILED DESCRIPTION

Figure 1:
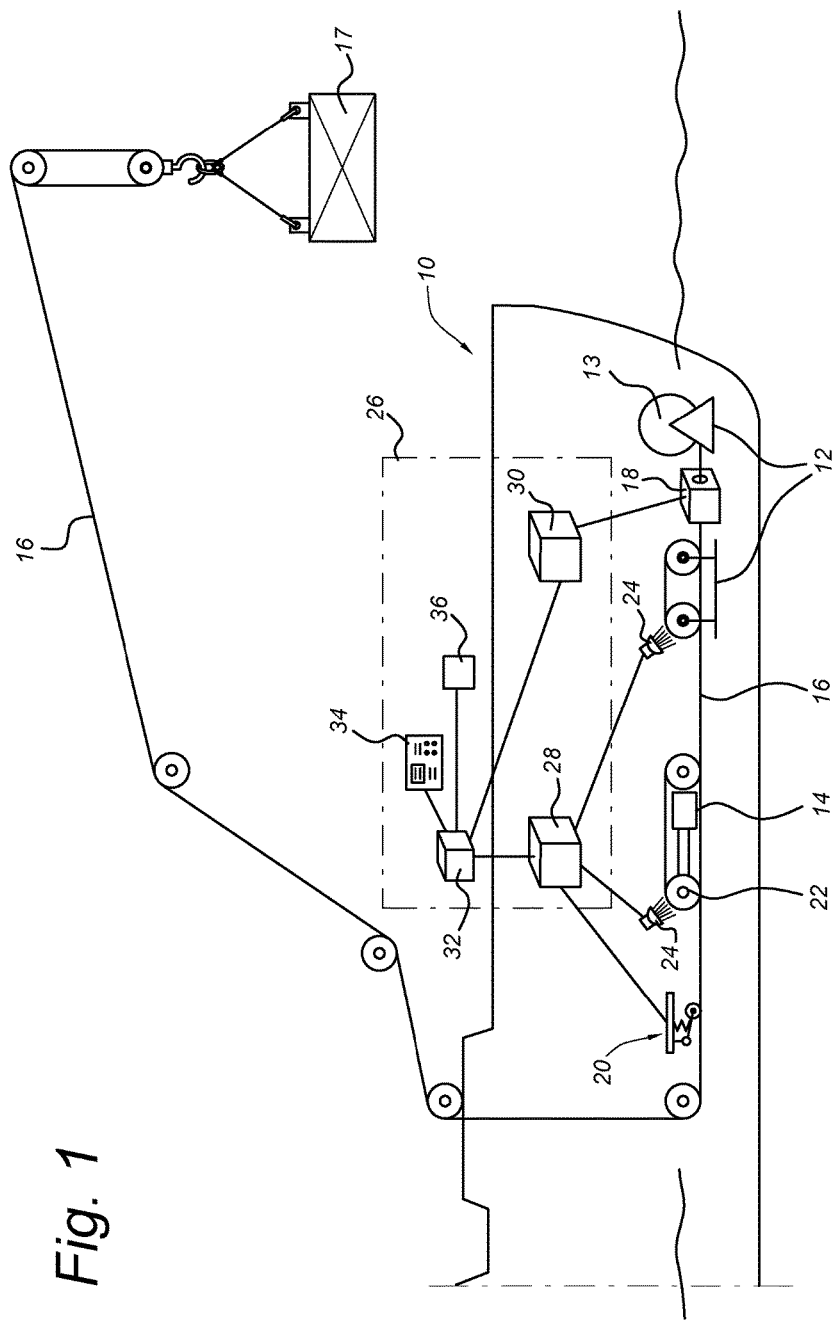
FIG. 1 schematically illustrates an example rope monitoring and analysis system.

FIG. 1 schematically illustrates rope monitoring and analysis system 10 in use with lifting system 12 and active heave compensation ("AHC") system 14 for rope 16 to raise and lower load 17. Rope monitoring and analysis system 10 includes rope data sensor 18, position measurement device 20, tension sensor 22, temperature sensors 24 and computer system 26. Computer system 26 includes lifting system processor and database 28, rope data sensor processor and database 30, overall processor and database 32, human machine interface 34 and external data input 36.

In the embodiment shown, lifting system 12 includes sheave 13. In other systems, lifting system 12 can include one or more winches and/or from zero to two sheaves. Sheave 13 of lifting system 12 are mounted on the vessel and crane to guide and bend rope 16 from lifting system 12 to lifting systems hook.

Rope 16 is a rope made of a plurality of strands. Rope 16 can be made of wire strands, for example steel wire, or can be made of fiber strands. In some cases, grease is used between the strands of the wire. Different sensors 18, 20, 22, 24 may be used depending on the material forming rope 16.

AHC system 14 is often used in offshore systems where water depths range from about 40 to about 3000 meters. AHC systems are especially useful in systems where the water depth is very deep, for example, 2-3 kilometers, and when used with voluminous and/or large objects to assist in a smooth transition a few meters before touchdown on the seabed or in a splash zone. AHC system 14 compensates for the motion of the vessel on the waves (or for the waves in the case of lowering through the splash zone), keeping load 17 motionless with regard to a fixed position such as the seabed. The compensation movements by AHC system 14 results in a friction in rope 16, and particularly between strands making up rope. This friction can heat up rope 16 and can cause the grease in rope 16 to melt off and/or cause other fatigue problems.

Rope data sensor 18 can be a cross-sectional measurement device such as a contactless electromagnetic wire rope inspection sensor, for example, the LMA-Test system manufactured by NDT Technologies, Inc. in South Windsor, Conn. In other embodiments, rope data sensor 18 can be another type of sensor and/or can measure the physical state, elongation, creep and/or appearance of the rope through other means. In the embodiment shown in FIG. 1, rope data sensor 18 is connected to rope 16 within lifting system 12. This ensures that any rope 16 running through lifting system 12 for use is monitored by rope data sensor 18 so that a physical property indicating rope status is sensed and sent to computer system 26.

Tension sensor 22 measures the tension in rope 16, and temperature sensors 24 measure the temperature at a bending point of rope 16. Other embodiments can have more or fewer rope usage sensors to collect other data regarding usage of the rope, for example, diameter and/or shape of the rope. Some systems 10 can include sensors related to outside factors, such as the sea state or weather conditions in which vessel is working during operations.

Position measurement device 20 can be a rope speed/sectional displacement sensor, a measuring wheel, or another type of position sensor such as a contactless measuring system. Position measurement device 20 works so that measurements taken by rope data sensor 18 and usage sensors 22, 24 can be accurately tracked and designated to correspond to a particular section of rope 16.

Computer system 26 can include a number of processors and/or databases to receive information from sensors 18, 22, 24 and from position measurement device 20, store that information, analyze it and use it for planning for usage, maintenance and/or replacement of all or sections of rope 16. In the example shown in FIG. 1, computer system 26 includes a rope data sensor processor and database 30 to process and store data from rope data sensor 18; a lifting system processor and database 28 to process and store data from position measurement device 20, tension sensor 22 and temperature sensors 24; and overall processor and database 32 to receive input from a rope data sensor processor 30 and lifting system processor and database 28. Overall processor and database 32 can also receive input at external statistical data input 36. This input data can be, for example, data from historic use of rope 16 or another rope and/or data from tests performed on rope 16 or another rope. Interface 34 is connected to overall processor and database 32, and can be used to control computer system 36 and rope monitoring and analysis system 10. Interface 34 can be used for various tasks including, controlling rope 16; monitoring rope 16 in real-time; predict maintenance and/or replacement schedules for a portion or all of rope 16; analyzing data and/or generating reports on data collected. Computer system 26 can receive and/or store data regarding rope 16 per section of rope 16 for the entire working length, for one or more particular sections of rope 16 (for example, heavily used sections), and/or for any number of sections for which there is useful data.

Rope monitoring and analysis system 10, through the use of a rope data sensor 18, a number of rope usage sensors 22, 24, a position measurement device 20 and computer system 26 allow for accurate analysis and monitoring of rope 16 for a real-time indication of the condition of one or more sections of rope 16 at any point in time. In past offshore and onshore operations using multi-strand ropes, the ropes were typically visually inspected or a measurement of rope cross-sectional area was taken at a specific point in time. This measurement could be taken using a device through which the rope passed, and the device was able to detect weakening and/or defects based on measurements of the rope passing through the device. This single data point inspection (correlated with classification society guidelines to guarantee safety of the systems) was then used to predict when a rope needed replacement. This past method often resulted in prematurely replacing the rope as a conservative measure to prevent catastrophic failure, and lead to high materials and replacement costs.

By using rope monitoring and analysis system 10, continuous real-time data collection of a physical property of rope 16 can be taken and correlated with data continuously collected regarding usage of the rope 16 and/or environmental conditions during usage of rope 16 to give a real-time indication of the condition of a section of the rope 16 at any point in time. Additional input regarding other statistical and/or test data could also be contributed if desired. The data in computer system 26 can then be used to extend the life of the rope 16, maintain safety during operations using rope 16 and decrease materials and replacement costs by being able to indicate when replacement of some or all of rope 16 is needed. The data and correlation can also be used to predict wire condition, the useful life of the rope 16, and maintenance or replacement schedules of some or all of rope 16. Additionally, data can be compiled and stored for future use in prediction of condition, maintenance and/or replacement schedules in relation to use and/or usage events for one or more sections of rope 16 or other ropes.

Figure 2:
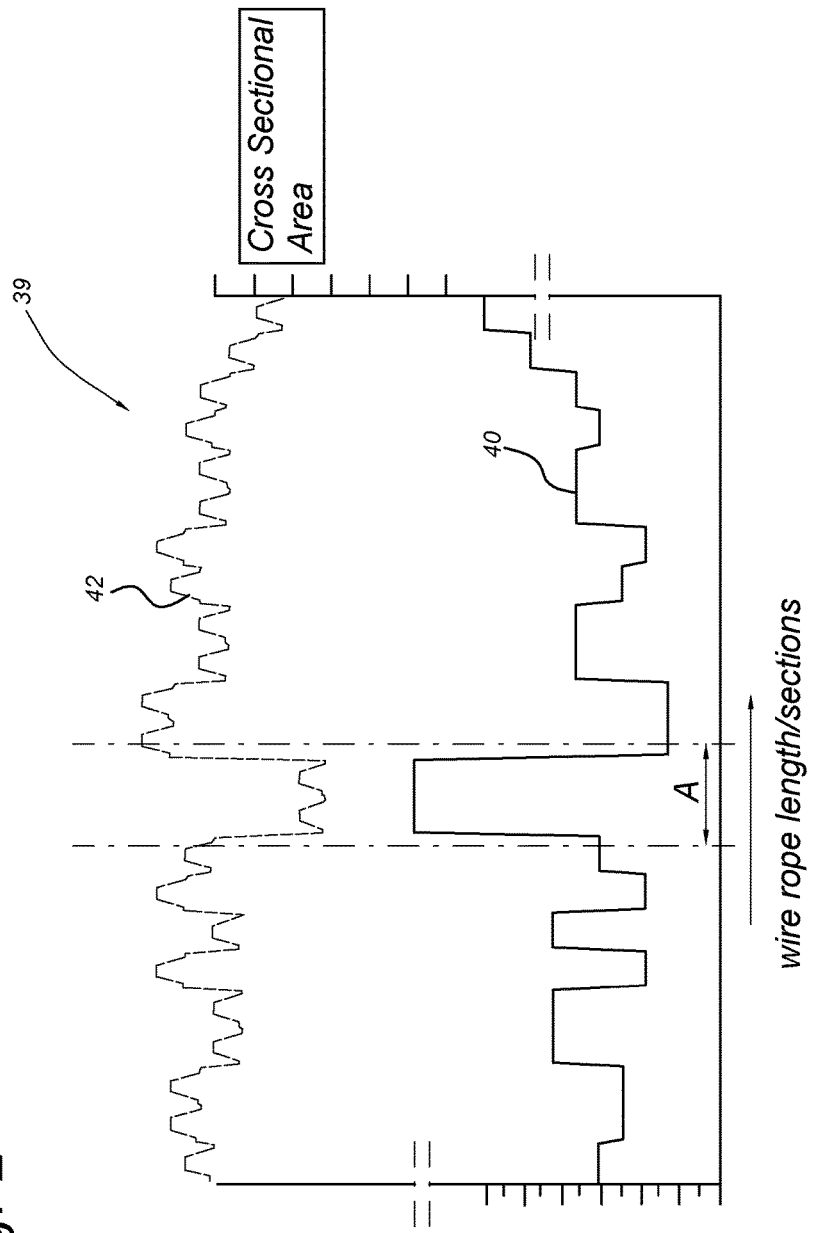
FIG. 2 shows an example data output plot from the rope monitoring and analysis system.

FIG. 2 shows an example data output plot 39 from the rope monitoring and analysis system 10, and includes lifting system operational data algorithm output 40 and cross-sectional area output 42. Along the x-axis is the rope length or sectional displacement, thus correlating measurements (and algorithm output from sensor data) to a section of rope 16.

Cross-sectional area output 42 shows a measurement of the cross-sectional area of rope 16 at each point along rope 16. This data is from rope data sensor 18, and gives a measurement of the cross-sectional area and therefore overall strength of each point along rope 16.

System operational data algorithm output 40 is formed by collecting data regarding tension, bends and temperature of rope 16 at each point. This is collected by one or more usage sensors, depicted in FIG. 1 as tension sensor 22 and temperature sensor 24. In other reports, data regarding tension, bending, temperature or any other property measured could be graphed separately on plot 39. The algorithm to integrate the data and form output 40 can be developed using data collected by system 10, historic data stored regarding rope 16 and/or other similar ropes and/or data input into computer system 26.

By plotting out cross-sectional area and operational or usage data against length of rope 16, a correlation between usage events and rope cross-sectional area can be seen, for example, at point A along rope's length, it can be seen that there is a high portion on lifting system operation data output 40. This could correspond to a section of the rope that had high tension forces and/or high temperatures. For example, this could correlate to a zone when load 17 is about to touch down to seabed for a particular operation. At this point, AHC system 14 typically works very hard to ensure a smooth transition for load 17 touchdown. This can result in a high temperature and a great deal of tension and/or bending at that point of rope 16. As can be seen from the graph of cross-sectional area 42, there is a dip in the cross-sectional area at point A. Thus, one or more strands of rope 16 may have snapped at this point due to stresses from operations. This could be a point where rope 16 needs replacement immediately or in a short time period based on comparison with a threshold point for cross-sectional area that the rope 16 must maintain to be in a safe-condition. Additionally, this data could tell a user to avoid this section of rope when other intense operations are being carried out and try to concentrate any future intense operations on areas of the rope 16 that have a higher cross-sectional area as shown by plot 42.

As the data regarding rope 16 usage is logged and stored in one or more databases in computer system 26, it can be accessed and used to predict what usage will likely lead to a reduction in cross-section area at or below a threshold indicating a need for replacement. For example, if it were logged that a particular number of bends and a particular amount of tension was recorded at a particular point, the operator could look to future operations to predict the reduction in cross-sectional area at any point based on the expected job parameters. This could then be used to plan maintenance or replacement operations that correlate with the actual status and usage of the rope and not simply a set period of time (as done in past systems).

In summary, by collecting, storing, correlating and/or analyzing data related to rope 16 condition and usage, rope monitoring and analysis system 10 is able to display real-time data on rope 16 condition and to use that data to predict and schedule maintenance and/or replacement schedules. As actual rope 16 status data is tracked and analyzed, this can result in a system able to avoid catastrophic events and conserve resources by only replacing all or a portion of rope 16 when necessary. This can also help to better predict the status and condition of rope 16 after future operations and to plan maintenance operations, keeping operational downtime due to maintenance at a minimum.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the appended claims.

The invention claimed is:

1. A system to monitor and analyze a multi-strand rope, the system comprising:
   a rope data sensor to collect data regarding the physical state of the rope;
   one or more usage sensors to collect data regarding the usage of the rope;
   a position measurement device to measure the position of the rope; and
   a computer system connected to the rope data sensor, the one or more usage sensors and the position measurement device to correlate the collected data and position measurement to give real-time data on the status of the rope at one or more sections.

2. The system of claim 1, wherein the computer system comprises
   one or more processors and/or databases for storing and/or processing data.

3. The system of claim 1, wherein the rope data sensor senses one or more of the cross-sectional area of the rope and the volume of the rope.

4. The system of claim 1, wherein the data regarding the usage of the rope includes one or more of the following: bending of the rope, tension in the rope, temperature of the rope, diameter of the rope, shape of the rope, elongation and creep of the rope.

5. The system of claim 1, wherein the position measurement device is a measuring wheel or a contactless measuring system.

6. The system of claim 1, wherein the computer system uses the data and the status to predict a failure of at least a section of the rope.

7. The system of claim 1, wherein the computer system uses the data and the status to plan maintenance for at least a section of the rope.

8. The system of claim 1, wherein the one or more usage sensors comprises a temperature sensor, a load sensor, a bending sensor, a speed sensor, a position sensor and/or a diameter sensor.

9. The system of claim 2, wherein the database includes information regarding the historic usage, the historic state and/or the current state for one or more sections of the rope.

10. The system of claim 1, wherein the rope is a wire rope.

11. The system of claim 1, wherein the rope is a fiber rope.

12. The system of claim 1, wherein the computer system comprises a user interface.

13. The system of claim 1, wherein the computer system comprises a data input for inputting data into system.

14. A method for real-time monitoring and analysis of a rope, the method comprising:
   measuring and collecting physical property data for the rope;
   measuring and collecting usage data for the rope;
   measuring the position of the rope; and
   correlating the physical property data, the usage data and the position to give a real-time measurement of the status and event history of the rope at one or more sections of the rope.

15. The method of claim 14, wherein the step of measuring and collecting physical property data for the rope comprises:
   measuring and collecting cross-sectional area data for the rope.

16. The method of claim 14, wherein the step of measuring and collecting usage data for the rope comprises:
   using one or more sensors to measure and collect data related to one or more of the following:
   bending of the rope, tension in the rope, temperature of the rope, speed of the rope, elongation or creep of the rope, diameter of the rope and shape of the rope.

17. The method of any of claim 14, and further comprising:
   storing and/or processing the data in a computer system.

18. The method of any of claim 14, and further comprising:
   predicting when at least a section of the rope will fail based on the physical property data, the usage data and position.

19. The method of claim 18, wherein the step of predicting when at least a section of the rope will fail based on the physical property data, the usage data and position comprises:
   comparing the physical property data for the rope with a predetermined failure threshold; and
   predicting when this threshold will be reached based on collected usage data and physical property data.

20. The method of claim 14, and further comprising:
   using the data collected, stored and/or input to form an algorithm which integrates and plots the collected, stored and/or input data as a single value for one or more rope sections.

* * * * *